United States Patent
Hansen

(10) Patent No.: US 6,971,516 B2
(45) Date of Patent: Dec. 6, 2005

(54) SHARPS CONTAINERS

(75) Inventor: Nick Hansen, Banbury (GB)

(73) Assignee: Owen Mumford Limited, Oxford (GB)

( * ) Notice: Subject to any disclaimer, the term of this patent is extended or adjusted under 35 U.S.C. 154(b) by 0 days.

(21) Appl. No.: 10/483,662

(22) PCT Filed: Jul. 11, 2002

(86) PCT No.: PCT/GB02/03182

§ 371 (c)(1),
(2), (4) Date: May 18, 2004

(87) PCT Pub. No.: WO03/006322

PCT Pub. Date: Jan. 23, 2003

(65) Prior Publication Data

US 2004/0188295 A1 Sep. 30, 2004

(30) Foreign Application Priority Data

Jul. 11, 2001 (GB) .................................. 0116874

(51) Int. Cl.[7] .............................................. B65D 83/00
(52) U.S. Cl. .................................... 206/366; 206/370
(58) Field of Search .............................. 206/364–366, 206/370, 63.5, 1.5, 210; 220/345, 346, 348, 220/254, 336, 326, 796–799; 604/110, 192, 604/263, 197, 198; 222/153, 480, 516, 548, 222/553; 229/7 SC, 907; 215/231, 354; 53/468

(56) References Cited

U.S. PATENT DOCUMENTS

| | | | | |
|---|---|---|---|---|
| 4,255,996 A | * | 3/1981 | Choksi et al. | ................. 83/140 |
| 4,275,628 A | * | 6/1981 | Greenhouse | .................. 83/167 |
| 4,375,849 A | * | 3/1983 | Hanifl | .......................... 206/366 |
| 4,552,280 A | * | 11/1985 | Owen et al. | ................. 220/348 |
| 4,657,139 A | | 4/1987 | Hanifl | |
| 4,867,309 A | * | 9/1989 | Germain | ..................... 206/366 |
| 4,995,871 A | | 2/1991 | Sasaki et al. | |
| 5,069,667 A | * | 12/1991 | Freundlich et al. | .......... 604/110 |
| 5,323,902 A | | 6/1994 | Palmer et al. | |
| 5,356,385 A | * | 10/1994 | Latini | .......................... 604/110 |
| 5,588,966 A | * | 12/1996 | Atsumi | ........................ 604/110 |
| 6,062,001 A | | 5/2000 | Kunik | |
| 6,158,314 A | * | 12/2000 | Thead et al. | .................... 83/23 |

FOREIGN PATENT DOCUMENTS

| | | |
|---|---|---|
| EP | 0 367 422 | 5/1990 |
| GB | 2 192 382 | 1/1988 |
| GB | 2 254 787 | 10/1992 |

* cited by examiner

*Primary Examiner*—Mickey Yu
*Assistant Examiner*—Jerrold Johnson
(74) *Attorney, Agent, or Firm*—Young & Thompson

(57) ABSTRACT

When a syringe has been used, it can be entered, needle tip first, down into a spigot (10) until the skirt of the needle assembly plugs firmly into the spigot, being held by ribs (12). The capsule can then be worked free and removed. Thereupon, a cover (14) is rotated in either direction and one of a pair of lugs (16) enters an adjacent slot (13) in the spigot (10). As the cover (14) is turned further, the lug (16) acts as a wedge and forces the needle assembly down. As the lug passes across the spigot (10), it finally presses the needle assembly clear, and that assembly drops into the main body of the container.

5 Claims, 1 Drawing Sheet

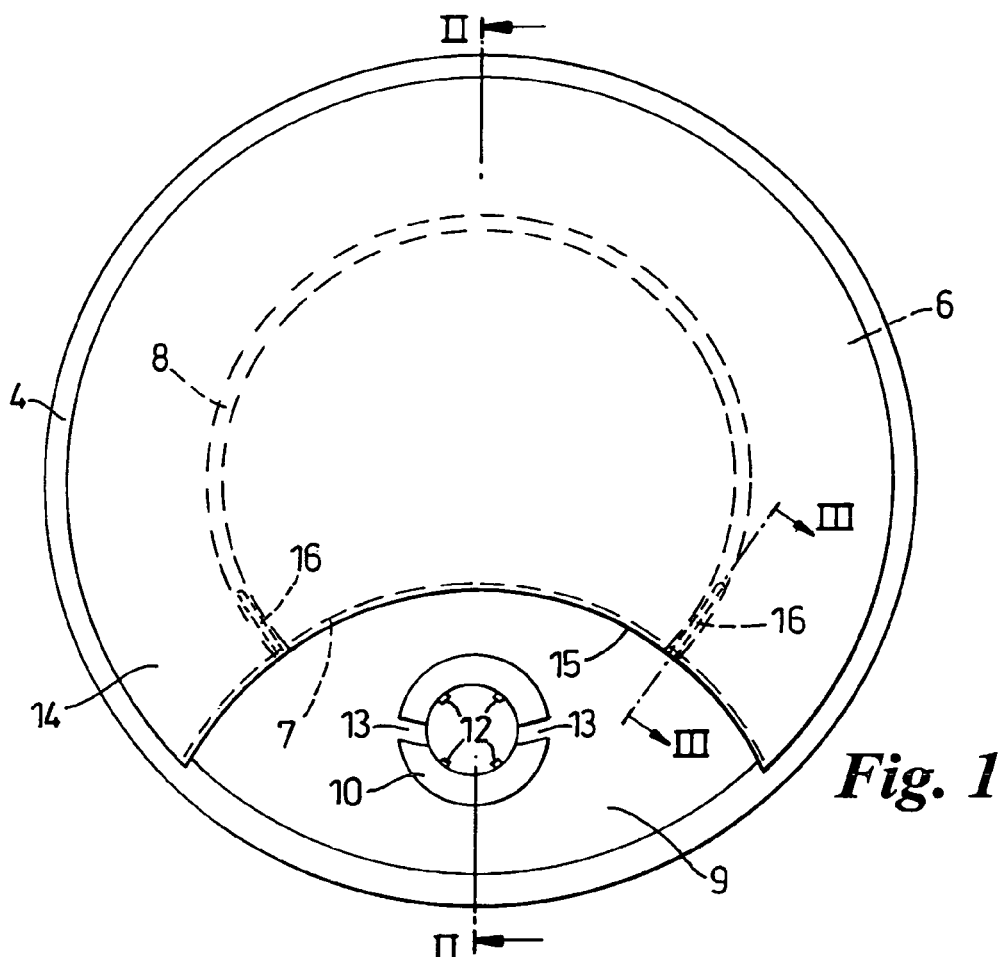
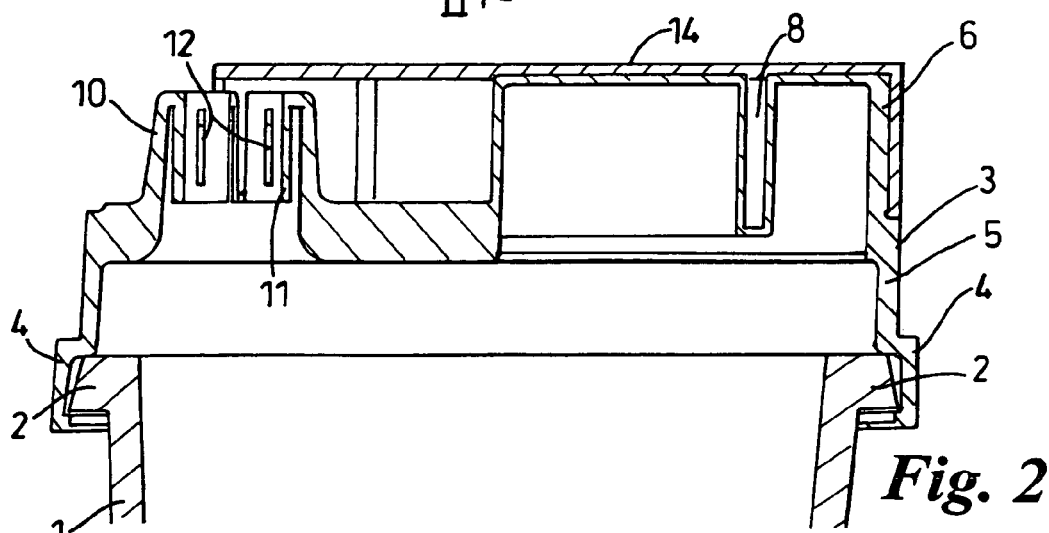
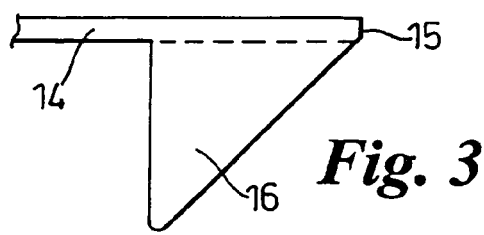

SHARPS CONTAINERS

This invention relates to sharps containers. It is concerned with those in which syringe needles are disposed.

A medical syringe has a tubular capsule with a plunger operable from its rear end and a head at its forward end to receive a needle assembly. The needle is double-ended, the rear end being co-axial within a skirt that retentively fits over the head. As the assembly is mated with the capsule, the rear end of the needle pierces a membrane across the top of the head and enters the dose contained in the capsule. After use, the needle has to be disposed of into a sharps bin, ideally without any need for the user to touch the needle assembly.

These needles are usually supplied in a disposable sterile container which has internal ribs to grip the skirt whilst it is being screwed to the syringe. It is therefore possible to apply quite a large tightening torque. But if after use of the syringe the needle container has already been lost or discarded, it can be difficult or impossible to remove the needle without using a tool.

It is the aim of this invention to adapt a sharps bin, which is going to be needed in any event, so that it can provide such a tool and streamline the operation of removing and safely concealing a used needle.

According to the present invention there is provided a sharps container having a captive cover movable between positions opening and closing an aperture which can be plugged by the skirt of a needle assembly of the kind described, the aperture having a lateral opening through which a wedge element on the underside of the cover can pass to traverse the aperture as the cover is moved to the closing position and thereby urge a needle assembly plugged into the aperture down in to the container.

Conveniently, the cover movement will be rotary, the aperture being offset from the axis of rotation. There may then be two opposed lateral openings at the same radius from that axis and two opposed wedge elements so that each element can pass completely across the aperture. It then does not matter which way the cover is turned.

For a better understanding of the invention one embodiment will now be described, by way of example, with reference to the accompanying drawing, in which:

FIG. 1 is a plan view of a sharps container,

FIG. 2 is a section on the line II—II of FIG. 1, and

FIG. 3 is a section to an enlarged scale on the line III—III of FIG. 1.

The container has a cup-like main body 1, only the upper part being shown, with an outwardly projecting annular rim 2 around its mouth. A lid 3 is made captive to this by its hooked annular flange 4 being snap fitted on using the inclined outer face of the rim 2. The lid 3 is a complex structure and not a simple body of revolution. Immediately above the hooked annular flange 4 it steps inwardly and upwardly into a shallow cylindrical wall 5 and then develops into two distinct formations. One of these is in the form of an inverted dish 6 with a bite 7 out of its side, appearing in plan view as a partially eclipsed disc. Co-axial with the part-cylindrical wall of this formation 6 and inset from it there is a deep narrow groove 8 opening at both ends into the bite 7. Symmetrically positioned on the platform 9 created by the bite 7, the other formation is an upstanding spigot 10, its mouth having a re-entrant skirt 11 with internal ribs 12. But the spigot is not a complete cylindrical member; at diametrically opposite positions, on the same radius from the axis of the container as the radius of the groove 8, there are vertical slots 13.

A cover 14 snap fits over this lid and bears on the top of the formation 6. In plan view it is similar to that formation, having an arcuate cut-out 15, so that it can rotate to expose the spigot 10 and the surrounding platform 9. But on its underside, at the edge of the cut-out 15, there are two downwardly projecting triangular lugs 16 at the same radius from the axis of the container as the groove 8 and the slots 13. These act as wedges as described below, and they can freely pass along the groove 8 as the cover is rotated.

When a syringe has been used, it can be entered needle tip first down into the spigot 10 until the skirt of the needle assembly plugs firmly into the spigot. The cover 14 has of course first been turned to expose it. With the skirt of the needle assembly held more firmly by the ribs 12 than its grip on the capsule, the latter can be worked free and removed. Thereupon, the cover 14 can be rotated in either direction and one of the lugs 16 enters the adjacent slot 13. As the cover 14 is turned further, the lug 16 acts as a wedge and forces the needle assembly down. As the lug passes across the spigot 10, it finally presses the needle assembly clear, and that assembly drops into the main body 1 of the container.

Provision may be made for the cover 14 to be retained quite firmly by snap action in a position closing off the spigot 10, which can remain concealed at all times except when actually being used.

While a rotary cover is perhaps the most convenient construction, it would be possible to have a cover that slides back and forth linearly.

The purpose of having the spigot 10 upstanding on the platform 9 and set apart from the formation 6 is to accommodate certain types of injection devices.

What is claimed is:

1. A sharps container for use in the disposal of a needle assembly having a skirt for being removably attached to a medical syringe, said container having a wall region defining an aperture which can be plugged by the skirt of a needle assembly, and a capture cover moveable between positions opening and closing said aperture, the wall region defining said aperture having a lateral opening through which a wedge element on the underside of the cover can pass to traverse the aperture as the cover is moved to the closing position and thereby urge the needle assembly plugged into the aperture down into the container.

2. A sharps container according to claim 1, wherein the cover movement is rotary, the aperture being offset from the axis of rotation.

3. A sharps container according to claim 2, wherein there are two opposed lateral openings at the same radius from said axis and two opposed wedge elements so provided that each element can pass completely across the aperture.

4. A sharps container, comprising:
  a wall region defining an aperture which can be plugged by a skirt of a needle assembly;
  a capture cover moveable between positions opening and closing said aperture;
  the wall region defining said aperture having a lateral opening through which a wedge element on the underside of the cover can pass to traverse the aperture as the cover is moved to the closing position and thereby urge the needle assembly plugged into the aperture down into the container.

5. A sharps container for use in disposal of a needle assembly having a skirt removably attached to a medical syringe, said container comprising:
  a wall region defining an aperture which can be plugged by the skirt of a needle assembly;

a capture cover moveable between positions opening and closing said aperture; and
a lateral opening with the wall region,
wherein the lateral opening allows a wedge element, on the underside of the cover, to traverse the aperture as the cover is moved to the closing position and thereby urge the needle assembly plugged into the aperture down into the container.

* * * * *